United States Patent [19]

Murphy et al.

[11] Patent Number: 5,015,765

[45] Date of Patent: May 14, 1991

[54] PROCESS FOR ISOLATING HYDROXAMIC ACIDS

[75] Inventors: Gerald J. Murphy, Morrisville, Pa.; John W. Ager, Princeton, N.J.; Matthew I. Levinson, Chicago, Ill.

[73] Assignee: FMC Corporation, Philadelphia, Pa.

[21] Appl. No.: 411,194

[22] Filed: Sep. 20, 1989

Related U.S. Application Data

[63] Continuation of Ser. No. 172,996, Mar. 24, 1988, abandoned, which is a continuation of Ser. No. 873,567, Jun. 12, 1986, abandoned.

[51] Int. Cl.$^5$ .............................................. C07C 83/10
[52] U.S. Cl. .................................................... 562/621
[58] Field of Search ........................................ 562/621

[56] References Cited

U.S. PATENT DOCUMENTS

| | | | |
|---|---|---|---|
| 2,168,305 | 8/1939 | Lippincott | 260/500.5 H |
| 2,772,281 | 11/1956 | Holly et al. | 260/500.5 H |
| 3,121,113 | 2/1964 | Bernstein et al. | 260/500.5 H |
| 3,154,578 | 10/1964 | Kinnel et al. | 260/500.5 H |
| 3,209,026 | 9/1965 | Finkelstein et al. | 260/500.5 H |
| 3,247,197 | 4/1966 | Gaeumann et al. | 260/500.5 H |
| 3,586,713 | 6/1971 | Buu-Hoi et al. | 260/500.5 H |
| 3,919,360 | 11/1975 | Collins | 260/500.5 H |
| 4,000,171 | 12/1976 | Kablaoui | 260/500.5 H |
| 4,092,430 | 5/1978 | Sellmann et al. | 260/500.5 H |
| 4,405,357 | 9/1983 | Chang | 71/88 |

FOREIGN PATENT DOCUMENTS 513970  5/1976  U.S.S.R. ...................... 260/500.5 H

OTHER PUBLICATIONS

Pinfold et al, "Chemistry and Industry", 11-11-67, pp. 1917 and 1918.

*Primary Examiner*—J. E. Evans
*Attorney, Agent, or Firm*—Norman L. Craig; Mark A. Greenfield; Patrick C. Baker

[57] ABSTRACT

Hydroxamic acids are efficiently isolated from aqueous reaction media in which they are produced as solids by adding to the reaction mixture with agitation, a coalescing amount of a water insoluble organic liquid, such as a light hydrocarbon or halohydrocarbon, which is a non-solvent for the hydroxamic acids. The coalesced particles float to the surface of the medium leaving behind a clear, aqueous phase which can be drained from the reaction vessel to leave the discrete particles of hydroxamic acid. Buoyancy of the particles is assisted by adding hydrogen peroxide to the reaction mixture or by bubbling air therethrough, usually after the coalescence.

6 Claims, No Drawings

PROCESS FOR ISOLATING HYDROXAMIC ACIDS

This application is a continuation, of application Ser. No. 172,996, filed Mar. 24, 1988 which is a continuation of Ser. No. 873,567 filed June 12, 1986, both now abandoned.

TECHNICAL FIELD

This invention relates to processes for separating and isolating solid hydroxamic acid products from aqueous reaction media.

BACKGROUND OF THE INVENTION

Hydroxamic acids are organic compounds containing the

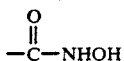

radical and are prepared by the SchottenBauman reaction, typified by the reaction between a hydroxylamine and a propionyl chloride in an aqueous medium in the presence of an acid acceptor to form a propionamide, e.g., the reaction between a hydroxylamine acid salt (sulfate or hydrochloride) and a 3-halo-2,2-dialkylpropionyl halide such as 3-chloro-2,2-dimethylpropionyl chloride in the presence of a base to form solid 3-chloro-N-hydroxy-2,2-dimethylpropionamide as described in Example 30 of U.S. Pat. No. 4,405,357 to J. H. Chang:

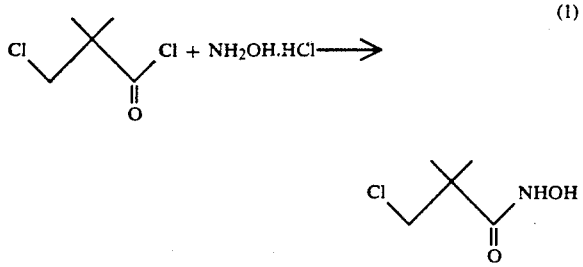

The product of this reaction (1) and a wide variety of other hydroxamic acids described in the Chang patent are intermediates for preparing various organic compounds including herbicidally active 3-isoxazolidinones, also as described in the Chang patent. The disclosure of the Chang patent is incorporated herein by reference.

Isolation of solid hydroxamic acid from the aqueous reaction medium by conventional procedures is a cumbersome, lengthy and often risky task because the product is produced as a finely dispersed solid, in many cases having the consistency of a thick slurry or paste. When it is attempted to isolate the product by batch centrifugation, for example, large portions of the solid material bypass the centrifuge, necessitating recycle of centrifugate back through the reactor. In addition, cake dewatering rates are highly variable and failure of transport and centrifuge equipment may be experienced, in turn requiring manual removal of product by operators wearing protective clothing and air masks. These problems result in significantly decreased productivity and increase the risk of contamination of work areas.

In the article "Flotation of Organic Precipitates" by T. A. Pinfold and E. J. Mahne, Chemistry and Industry, November 11, 1967, pages 1917–1918, methods for separating precipitates by flotation are described, including the flotation of insoluble, cyclic, organic compounds (such as may be contained in small amounts in a large bulk of solution) by first dissolving the compound in ethanol and then adding the alcohol solution to water. The compound then precipitates, floats and can be removed from the surface by gentle suction.

As will become apparent from the description following, the solubility of ethanol in an aqueous medium and the highly dilute character of the system prevents successful application of the Pinfold and Mahne technique to the isolation of hydroxamic acids. The technique as described in the article is thus limited to the concentrating of cyclic organic compounds in highly dilute solutions, rather than the removal of water, as in the present invention from more highly concentrated mixtures containing hydroxamic acid reaction products, resulting in efficient isolation of the hydroxamic acids.

SUMMARY OF THE INVENTION

It has now been found that by adding with agitation to an aqueous reaction mixture containing a hydroxamic acid product and, optionally but usually, residual hydroxylamine or a hydroxylamine acid salt, a water insoluble organic liquid which is a nonsolvent for the hydroxamic acid product, the hydroxamic acid solids coalesce into discrete particles such as prills. The particles are buoyant and float to the surface of the reaction mixture, leaving behind a clear aqueous phase. The aqueous phase is then readily separated by draining. The product particles may then be removed or subjected in place to further purification or to chemical reaction.

The invention thus reduces cycling time in the synthesis of hydroxamic acids, eliminates time consuming and costly centrifugation and/or filtration steps, and contributes significantly to safety by eliminating need for manual handling of product.

In other aspects of the invention, the buoyancy of the hydroxamic acid product is increased by the addition of hydrogen peroxide and/or air to the reaction mixture. The peroxide-generated oxygen or air bubbles buoy the hydroxamic acid particles to the surface. Alternatively, the peroxide or air decomposes residual hydroxylamine to form gases which buoy the hydroxamic acid particles to the surface.

DETAILED DESCRIPTION

The isolation process of the invention is practiced by adding, preferably incrementally, to the aqueous reaction medium, resulting from a SchottenBauman synthesis and containing a solid hydroxamic acid reaction product, amounts of a water insoluble organic liquid which is also a non-solvent for the hydroxamic acid, while the reaction medium is agitated in a conventional manner. The reaction mixture is relatively concentrated, e.g., total reaction product solids in a reaction mixture containing 3-chloro-N-hydroxy-2,2-dimethylpropionamide will usually range from about 1% to about 50% by weight, exclusive of non-solvent additive, preferably about 5–30% on the same basis. Concentrations of reaction mixtures containing other hydroxamic acids may, of course, differ from these ranges due to different synthesis conditions, products and yields.

As the organic liquid is added, the finely divided hydroxamic acid particles begin to coalesce to form discrete particles or prills, typically of the order of about 1–5 mm in diameter. When the agitation is terminated, the coalesced particles rise to the surface of the medium and float at or near the surface, leaving behind a clear aqueous phase which can be conveniently drained from the reaction vessel through a retaining screen, leaving behind the coalesced hydroxamic acid particles. If desired, the particles may be further purified by dispersion in water and repetition of the coalescence, or the redispersed hydroxamic acid may be treated as described in the Chang patent for direct conversion to isoxazolidinone compounds.

The conditions of treatment of the hydroxamic acid-containing reaction medium may be varied in accordance with the specific hydroxamic acid being isolated and the requirements of subsequent reaction steps, if the isolation is part of an overall reaction scheme. Agitation of the reaction mixture during addition of the coalescing organic liquid is important for good distribution of the liquid throughout the mixture and for good contact with the hydroxamic acid particles. In the case of an axial blade turbine stirring device, effective agitation is achieved at about 300–800 RPM but the speed will depend, of course, on the scale of the procedure, higher agitation being possible on a laboratory scale but lower agitation being preferred in a commercial reactor. Other means of agitation may, of course, be employed, as are conventional in chemical synthesis and separation.

Likewise, the amount and rate of addition of the coalescing agent will depend on various parameters and may be varied accordingly. Typically, for isolation of a hydroxamic acid such as 3-chloro-N-hydroxy-2,2-dimethylpropionamide, about 25–80 mole percent of the coalescer, based on the 3-chloro-2,2-dimethylpropionyl chloride precursor, will be effective, more preferably about 35–60 mole percent. The coalescer may be added to the reaction medium above or below the surface, while the medium is agitated, preferably in incremental amounts over about several minutes to several hours, e.g., 5–60 minutes and possibly up to about 8 hours, depending on the scale of the treatment.

Reaction mixture temperature and pH during addition of the coalescing agent are not critical, and typically will be about 20°–40° C., preferably 25°–32° C., at a pH of 4–8, preferably 6–7.5. An advantage of the isolation procedure is that no substantial adjustments in temperature or pH of the reaction product mixture obtained in the synthesis of the hydroxamic acid are required. Upon completion of addition of the coalescer, it is useful to continue the agitation for a period of time to stabilize the coalescence. Typically, such agitation may be at a lower mixer speed and may be effected for about 0.25 to 8 hours, preferably about 0.5–2.0 hours.

The buoyancy of the hydroxamic acid coalesced or coalescing particles may be assisted by various techniques, including either or both of (1) adding hydrogen peroxide to the reaction mixture and (2) passing air through the reaction mixture, preferably while the reaction mixture is being agitated or subsequent to the agitation. Typically, addition of about 0.5–2.0% by weight of 30% hydrogen peroxide and sparging of the reaction mixture with a gentle stream of air will be effective, but such conditions may be varied as desired for best effect. In either approach, the resultant bubbles (either from the hydrogen peroxide or the air itself, or from gases generated by reaction between the hydrogen peroxide or air with residual hydroxylamine in the mixture) appear to collect on the coalesced hydroxamic acid particles to promote their flotation.

It is essential that the organic liquid be water insoluble as well as a non-solvent for the hydroxamic acid; otherwise, it will not effectively coalesce the hydroxamic acid particles (although it may promote concentration of the acid in an organic phase, in the manner of the Pinfold and Mahne process described above). Organic liquids which are non-solvents for hydroxamic acids typically will have low polarity, as measured by dipole moment. In the usual case, a dipole moment in the range of 0 to about 1.2 debyes is a good standard, although it will be recognized that this will depend on the particular hydroxamic acid to be isolated. In addition, it has been found that the coalescing action is largely independent of the specific gravity of the organic liquid. However, in the case of organic liquids having specific gravities over 1, it may be desirable to improve the buoyancy of the coalesced hydroxamic acid particles by one or more of the techniques described above.

A wide variety of organic liquids can be used as coalescing agents in accordance with the invention. Useful organic liquids of specific gravities less than 1 include the various light hydrocarbons, halohydrocarbons and petroleum ethers, including pentane, hexane, heptane, cyclohexane, methylcyclohexane, benzene, toluene, both low and high boiling petroleum ethers, and the like. Useful organic liquids with specific gravities over 1 include the various halohydrocarbons such as mixed chlorotoluenes, chlorobenzene, dichlorobenzenes such as ortho-dichlorobenzene, ortho-chlorobenzyl chloride, carbon tetrachloride, and the like. Mixtures of two or more of any of the organic liquids of course may be employed. Preferred organic liquids are the light hydrocarbons such as heptane, and ortho-chlorobenzyl chloride. The latter is preferred in those cases in which the isolated hydroxamic acid is to be treated with this reagent in downstream reactions since its use as a coalescer thereby eliminates need for removal and recycle in such downstream processing.

The following examples, in which all parts and percentages are by weight and all temperatures are ° C unless otherwise noted, will further illustrate the invention.

EXAMPLE 1

A two liter resin kettle was equipped with two inlet tubes, a thermometer, a pH probe, a cooling jacket, and an axial blade turbine stirring device. One of the inlet tubes was connected via a calibrated pump to a reservoir containing an aqueous 50% sodium hydroxide solution. The addition of the aqueous base to the reaction mixture was regulated by a pH meter/controller box connected to the pump and pH probe. The pH meter/controller box was set for a pH of 7.0–7.5, delivering aqueous base to the reactor to maintain the pH. The other inlet tube was connected via a calibrated pump to a reservoir containing 3-chloro-2,2-dimethylpropionyl chloride.

A solution of aqueous 30% hydroxylamine sulfate (755 grams, 1.34 moles–1.5 equivalents) was placed in the reactor. The solution was stirred and its pH adjusted to 7.5 with the aqueous base. Ethyl xanthic acid, potassium salt (1.0 gram, 0.006 mole) was added to the reaction mixture as an iron chelator in order to inhibit iron-catalyzed decomposition of unreacted hydroxylamine, which decomposition causes excessive foaming. (A floccing aid, 0.5 gram, was also added, but it was found to be unnecessary.) The viscous mixture was diluted with an additional 150 grams of water. The speed of the stirrer was adjusted to 600 RPM and the addition of 3-chloro-2,2-dimethylpropionyl chloride (286 grams, 1.85 moles-1.0 equivalent) was commenced. Throughout the addition the pH of the reaction mixture was maintained at 7.0-7.2 with the simultaneous addition of 50% aqueous base via the pH meter/controller box. The complete addition of acid chloride required approximately 2.5 hours during which time the reaction mixture temperature was maintained at 26°-28° C. Upon completion of addition, the speed of the stirrer was slowed to 300 RPM, and the viscous, foamy reaction mixture stirred for one hour.

Thereafter, the speed of the stirrer was increased to 1000 RPM and OCBC (ortho-chlorobenzyl chloride, 114 grams, 0.71 mole-38.3 mole percent based on acid chloride charged) was added during a five minute period. Upon completion of addition and a five minute stirring period, the viscous, foamy reaction mixture transformed into a heterogeneous mixture of semi-buoyant solid prills of 3-chloro-N-hydroxy-2,2-dimethylpropionamide and OCBC in a clear, liquid aqueous phase.

The reaction mixture was then stirred for 30 minutes more, the stirrer was stopped, and the kettle was fitted with a sintered glass gas bubbler. A gentle air flow was applied to the gas bubbler to further buoy the prilled solid in the clear aqueous phase. The gas bubbler was then attached to a vacuum and the clear aqueous phase removed. The yield of recovered damp, prilled solid was 524 grams. Gas chromatographic analysis of the prilled solid indicated it was composed of 50% by weight of 3-chloro-N-hydroxy-2,2-dimethylpropionamide (262 grams, 1.73 moles, 93.4 mole percent yield based on acid chloride charged). The solid prills were found to contain less water than product isolated by centrifugation.

EXAMPLE 2

Essentially as described in Example 1, heptane, 65 grams (100 cc), was added to a stirred reaction mixture containing 3-chloro-N-hydroxy-2,2-dimethylpropionamide. Separation and flotation substantially equivalent to that of Example 1 resulted.

EXAMPLES 3-14

Essentially as described in Example 1 but with the differences indicated in Table 1 below, 3-chloro-N-hydroxy-2,2-dimethylpropionamide, formed by the reaction of 3-chloro-2,2-dimethylpropionyl chloride (CPC), 286 grams, 1.85 moles, and excess hydroxylamine sulfate, was isolated by coalescence and flotation by the addition of ortho-chlorobenzyl chloride (OCBC) to a vigorously agitated aqueous reaction mixture also containing residual, unreacted hydroxylamine sulfate. As a result of these examples, it was determined that an antifoaming agent, modification of pH and hydrogen peroxide/air addition were unnecessary for the success of the isolation, although (Examples 10-12) buoyancy of the hydroxamic acid prills could be improved by the hydrogen peroxide or air addition.

TABLE 1

SEPARATION OF 3-CHLORO-N-HYDROXY-2,2-DIMETHYLPROPIONAMIDE BY COALESCENCE AND FLOTATION

| Ex. No. | OCBC Added Amount/Moles | Mole Percent OCBC on CPC Charge | Comments |
|---|---|---|---|
| 3 | 203 g 1.26 moles | 68.1% | OCBC added in 20 ml portions. After 60 ml added, product was prilled solid. An additional 100 ml OCBC was added and the solid turned sticky. 100 ml water added to isolate sticky solid |
| 4 | 89.2 g 0.55 mole | 29.9% | Water, 70 ml, was added to mixture, along with 13 g of antifoam agent. Added 50 ml OCBC in one portion and the slurry coalesced. The mixture was stirred vigorously for 5 minutes and 20 ml OCBC added. After 5 minutes prilled solid floated to the surface; 479 g of oily cake isolated. |
| 5 | 152.0 g 0.94 mole | 51.0% | Antifoam agent, 30 g, was added to the stirred mixture followed by the addition of three portions of 33 ml each of OCBC during a 2 minute period. Mixture was stirred for 1 hour then an additional 20 ml of OCBC was added. Isolated 480.5 g of wet solid. |
| 6 | 76.2 g 0.47 mole | 25.4% | pH not adjusted. Antifoam agent, 15 g, was added and mixture stirred vigorously for 1.5 hours. Added 60 ml of OCBC with vigorous stirring during a 5 minute period. Stirring then stopped and prilled solid floated to the surface. The water was drained to yield 480 g of wet solid. |
| 7 | 76.2 g 0.47 mole | 25.4% | pH mixture adjusted to 8.0 and 15 g of antifoam agent added. Mixture was stirred vigorously for 10 minutes and 60 ml of OCBC added during a 10 minute period. Mixture was stirred slowly for 25 minutes then the stirring stopped. Prilled solid floated to the surface. The water was drained to yield 425 g of wet solid. |
| 8 | 165.6 g 1.0 mole | 55.6% | pH not adjusted. Antifoam agent, 15 g, was added with stirring. OCBC, 70 ml, was added with stirring during a 10 minute period. The slurry did not coalesce. An additional 15 g of antifoam agent was added, followed by 35 ml of OCBC. After stirring 5 minutes the slurry still did not coalesce. An additional 35 ml of OCBC was added during a 5 minute period and the slurry coalesced into prills. |
| 9 | 146.0 g 0.91 mole | 49.0% | pH not adjusted. OCBC, 60 ml, was added with stirring during a 10 |

TABLE 1-continued

SEPARATION OF 3-CHLORO-N-HYDROXY-2,2-DIMETHYLPROPIONAMIDE BY COALESCENCE AND FLOTATION

| Ex. No. | OCBC Added Amount/Moles | Mole Percent OCBC on CPC Charge | Comments |
|---|---|---|---|
| 10 | 165.6 g 1.0 mole | 55.6% | minute period. The slurry did not coalesce. Antifoam agent, 15 g, was added, with no appreciable coalescence. An additional 40 ml of OCBC and an additional 15 g of antifoam agent were added with no appreciable coalescence. An additional 15 ml of OCBC was added rapidly and the slurry coalesced into prills. The water was drained to yield 459 g of wet solid. Rate of addition of OCBC important to good coalescence. pH not adjusted. OCBC, 50 ml, containing 1 g of antifoam agent was added with medium speed stirring. The slurry did not coalesce. Three portions of OCBC, one of 30 ml and two of 20 ml were added before slurry coalesced into prills. The water was drained to yield 452 g of wet solid. |
| 11 | 152.0 g 0.94 mole | 51.0% | pH adjusted to 9.1 and after 5 minutes stirring, 120 ml of OCBC was added during a 5 minute period. To aid in flotation 15 ml of 30% $H_2O_2$ was added to the coalesced solid prills. Slow stirring was continued for 30 minutes after which time the prills rose to the surface. The prills were poured into a Buchner funnel and washed with 250 ml of saturated NaCl solution to yield 440 g of wet solid. |
| 12 | 127.0 g 0.79 mole | 42.6% | pH not adjusted. OCBC, 100 ml, was added during a 5 minute period. 6 ml of 30% $H_2O_2$ was then added and the mixture stirred for 30 minutes. The stirring was stopped and solid prills floated to the surface. The prills were collected by filtration and slurried with 250 ml of saturated NaCl solution to yield 400 grams of wet solid. |
| 13 | 114.0 g 0.71 mole | 38.3% | pH not adjusted. With vigorous stirring 90 ml of OCBC containing 1 g of antifoam agent was added over 20 seconds. The slurry coalesced immediately. Following a 5 minute stirring period a stream of air was introduced via a gas bubbler to buoy the solid prills. The water was drawn from the vessel under vacuum to yield 447 g of wet solid. |
| 14 | 114.0 g 0.71 mole | 38.3% | Same as Ex. 13 without the antifoaming agent. Isolated 453 g of wet solid prills. |

We claim:

1. A process for isolating a solid hydroxamic acid product from an aqueous reaction mixture optionally containing residual hydroxylamine or a hydroxylamine acid addition salt, which comprises adding to the reaction mixture with agitation a product coalescing amount of a water insoluble organic liquid which is a nonsolvent for the product and passing hydrogen peroxide and/or sparging air through the reaction mixture during the agitation or thereafter, whereupon the product coalesces into buoyant, discrete particles and a clear aqueous phase is formed, and separating the aqueous phase from the particles; said organic liquid selected from hydrocarbons, halohydrocarbons and any mixture thereof, and said hydroxamic acid being 3-chloro-N-hydroxy-2,2-dimethylpropionamide.

2. The process of claim 1 wherein the organic liquid has a dipole moment in the range of about 0-1.2 debyes.

3. The process of claim 1 wherein the organic liquid is selected from a petroleum ether, pentane, hexane, heptane, cyclohexane, methylcyclohexane, benzene, toluene, chlorotoluene, dichlorobenzene, chlorobenzyl chloride, carbon tetrachloride and a mixture of two or more thereof.

4. The process of claim 1 wherein the organic liquid has a specific gravity greater than 1.

5. The process of claim 1 wherein the organic liquid is ortho-chlorobenzyl chloride.

6. The process of claim 1 wherein the organic liquid is heptane.

* * * * *